United States Patent
Means

(10) Patent No.: US 7,105,312 B2
(45) Date of Patent: Sep. 12, 2006

(54) CA$^{2+}$/CALMODULIN-DEPENDENT PROTEIN KINASE IV

(75) Inventor: Anthony R. Means, Chapel Hill, NC (US)

(73) Assignee: Duke University, Durham, NC (US)

( * ) Notice: Subject to any disclaimer, the term of this patent is extended or adjusted under 35 U.S.C. 154(b) by 750 days.

(21) Appl. No.: 10/120,187

(22) Filed: Apr. 11, 2002

(65) Prior Publication Data

US 2003/0059854 A1 Mar. 27, 2003

Related U.S. Application Data

(60) Provisional application No. 60/282,898, filed on Apr. 11, 2001, and provisional application No. 60/322,438, filed on Sep. 17, 2001.

(51) Int. Cl.
*C12Q 1/48* (2006.01)
*C12Q 1/00* (2006.01)
*C12Q 1/37* (2006.01)

(52) U.S. Cl. ............... 435/15; 435/4; 435/23; 435/24; 424/529; 530/300

(58) Field of Classification Search ........... 435/15, 435/4, 23, 24; 424/529; 530/300
See application file for complete search history.

(56) References Cited

U.S. PATENT DOCUMENTS

| 6,403,352 B1 | 6/2002 | Poovaiah et al. ............ 435/194 |
| 6,436,656 B1 * | 8/2002 | Means ......................... 435/15 |

FOREIGN PATENT DOCUMENTS

WO    WO 98/39412    9/1998

OTHER PUBLICATIONS

Russell,J;Clinics inchest medicine;v7(2);pp189–200;(Jun. 1986) (Abstract Only).*

Kitani et al, "Inactivation of Ca$^{2+}$/Calmodulin–Dependent Protein Kinase IV by Ca$^{2+}$/Calmodulin and Restoration of the Activity by Mg$^{2+}$/EGTA", J. Biochem. 117:1070–1075 (1995).

* cited by examiner

*Primary Examiner*—Ralph Gitomer
(74) *Attorney, Agent, or Firm*—Nixon & Vanderhye P.C.

(57) ABSTRACT

The present invention relates to Ca$^{2+}$/calmodulin-dependent protein kinase IV (CaMKIV) and, in particular, to methods of screening compounds for their ability to act as CaMKIV agonists or antagonists. The invention further relates to compounds identified using such methods and to therapeutic methodologies based on same.

15 Claims, 15 Drawing Sheets

SEQUENCE LISTING

```
<160> NUMBER OF SEQ ID NOS: 16

<210> SEQ ID NO 1
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 1
cgttgcgtct gaagagtaga agttc                                            25

<210> SEQ ID NO 2
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 2
tgagagattt gccagggtca ac                                               22

<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 3
gtcttttggt ctctgcctcg tg                                               22

<210> SEQ ID NO 4
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 4
atgggcacat caccactaca cc                                               22

<210> SEQ ID NO 5
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 5
```
cccaacttca acgactccaa cc                                            22

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 6
cagagagaga gaaagagagc gagc                                          24

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 7
ggtgcccgac ctcttttttac                                              20

<210> SEQ ID NO 8
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 8
ctgaaactcc ccaggatgct c                                             21

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 9
ccgaacaact ctactatgaa actgtc                                        26

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Primer

<400> SEQUENCE: 10
atcggcattt tgaacgaggt c                                             21

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
gtcactacac ctgaacctga gtaag                                         25

<210> SEQ ID NO 12
<211> LENGTH: 22
<212> TYPE: DNA
<213> ORGANISM: Artificial Sequence -continued

```
<220> FEATURE:
<223> OTHER INFORMATION: Description of Artificial Sequence: Primer

<400> SEQUENCE: 12
aaaggagtcg ctgctgattc gg                                          22

<210> SEQ ID NO 13
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 13
cagtagccca catcagtgtc aaaag                                       25

<210> SEQ ID NO 14
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 14
gttggataca ggccagactt tgttg                                       25

<210> SEQ ID NO 15
<211> LENGTH: 23
<212> TYPE: DNA
<213> ORGANISM: Artificial Sequence
<220> FEATURE:
<223> OTHER INFORMATION: Description of Artificial Sequence: Primer

<400> SEQUENCE: 15
agcctatagg ccagcctacc ctc                                         23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 16
tttcctacta ccattcccca gccg                                        24
```

CA$^{2+}$/CALMODULIN-DEPENDENT PROTEIN KINASE IV

The present application claims priority from U.S. Provisional Application No. 60/282,898, filed Apr. 11, 2001, and Provisional Application No. 60/322,438, filed Sep. 17, 2001, the entire contents of both applications being incorporated herein by reference.

TECHNICAL FIELD

The present invention relates to Ca$^{2+}$/calmodulin-dependent protein kinase IV (CaMKIV) and, in particular, to methods of screening compounds for their ability to act as CaMKIV agonists or antagonists. The invention further relates to compounds identified using such methods and to therapeutic methodologies based on same.

BACKGROUND

Ca$^{2+}$/calmodulin-dependent protein kinase IV (CaMKIV) is a monomeric multifunctional enzyme that is expressed primarily in subanatomical portions of the brain, T lymphocytes and postmeiotic male germ cells. It is present in the nucleus of cells in which it is expressed (Jensen et al, Proc. Natl. Acad. Sci. USA 88:2850 (1991)). CaMKIV phosphorylates and activates the cyclic AMP response element binding proteins CREB and CREMτ in a manner analogous to protein kinase A (Matthews et al, Mol. Cell. Biol. 14:6107 (1994); Sun et al, Genes Dev. 8:2527 (1994); Enslen et al, J. Biol. Chem. 269:15320 (1994)).

In the absence of Ca$^{2+}$/calmodulin, CaMKIV is inactive. Activation requires three events: i) binding of Ca$^{2+}$/calmodulin; ii) phosphorylation of a single threonine residue present in the activation loop by a separate protein kinase that is also Ca$^{2+}$/calmodulin-dependent; and iii) autophosphorylation of serine residues present in the extreme N-terminus that is required to relieve a novel form of autoinhibition.

CaMKIV has previously been implicated in mediating cytokine gene transcription during T cell activation using a line of transgenic mice that overexpress a catalytically inactive form of CaMKIV (Anderson et al, Mol. Endo. 11:725–737 (1997)). Driven by the murine lck promoter, the mutant CaMKIV was expressed only in developing thymoctes and thus, the differentiation of mature T cells could not be addressed in these mice. High level expression of CaMKIV is restricted to only a few cell types, including the CD4+ T cell, where it has been localized to the nucleus in a tight 1:1 stoichiometric association with protein phosphatase 2A (Hanissian et al, J. Biol. Chem. 268:20055–20063 (1993), Westphal et al, Science 280:1258–1261 (1998)).

The specific role of CaMKIV in T cell activation is described in U.S. application Ser. No. 09/033,715, as is the importance of CaMKIV as a target for immunosuppressive agents. A method of identifying immunosuppressive agents that target CaMKIV is also provided in U.S. application Ser. No. 09/033,715. Agents identified using the screen provided there are T cell specific and thus substantially free of adverse side effects.

The studies described herein relate, at least in part, to the role of CaMKIV in CD4+ T cell differentiation. Naïve CD4+ T cells can differentiate along different pathways in response to stimulation by MHC/antigen complex (see FIG. 1). The most well characterized T helper subsets are referred to as Th1 and Th2 which differ in the types of cytokines they secrete. The different sets of cytokines in turn mediate different effector functions. Th1 cells secrete IL-2, INF-γ, and TNF-β. IL-2 functions as the Th1 cell autocrine growth factor and promotes the differentiation of CD8+ T cells into cytolytic T cells. IFN-γ stimulates macrophages to kill intracellular microbes and activates the production of IgG which is the principle immunoglobulin involved in opsonization and phagocytosis. The TNF-β secreted by Th1 cells recruits and activates inflammatory leukocytes. Collectively, these are mechanisms used by Th1 cells to promote elimination of intracellular microbes. In contrast, Th2 cells express IL-4, IL-5 and IL-13. IL-4 functions as the Th2 autocrine growth factor. This cytokine is also required for immunoglobulin switching to the IgE isotype and is the primary activator of mast cells. IL-5 stimulates eosinophils to kill parasites. IL-13 is required for generation of allergic asthma. Th2 cells thus function to eliminate parasites and are the mediators of allergic responses.

The mechanisms determining the pathway by which an individual, naïve T cell proceeds are unclear, but the process is strongly influenced by the context in which T cell stimulation occurs. Once a Th1 or Th2 population begins to become established, the cytokines it produces inhibit the alternative pathway (FIG. 1) to further promote dominance of a single cell type. In vivo, one or the other differentiated cell type generally comes to dominate during the course of an immune response to profoundly determine the outcome of the response.

The present invention provided methods of identifying agonists (activators) and antagonists (inhibitors) of CaMKIV and to methods of using compounds so identified in a variety of therapeutic settings.

SUMMARY OF THE INVENTION

The present invention relates to Ca$^{2+}$/calmodulin-dependent protein kinase IV (CaMKIV) and, in particular, to methods of screening compounds for their activity as CaMKIV agonists or antagonists. The invention further relates to compounds identified using the present methods and to therapeutic methodologies based on the use of such compounds.

Objects and advantages of the present invention will be clear from the description that follows.

BRIEF DESCRIPTION OF THE DRAWINGS

FIG. 2B, Secreted IL-2 was determined after stimulating CD4+ T cells for 3 days with plate-bound CD3 and CD28 antibodies. Bars represent means +/− SE. where n=5.

FIG. 3A, Following 5 days of stimulation with plate-bound CD3 and CD28 antibodies, CD4+ T cells were collected, washed, and restimulated for 1 day, at the end of which period secreted Th1 cytokines were quantitated. Bars represent means +/− S.E. where n=10. The asterisk denotes a statistically significant difference as determined by t-test (p value<0.05). FIG. 3B, Th2 cytokines were quantitated following the stimulation protocol described in FIG. 3A. FIG. 3C, CD4+ T cells were stimulated with CD3 and CD28 antibodies in the presence of exogenously added recombinant IL-4 (50 ng/ml). At the end of 5 days, the cells were collected, washed, and restimulated for 1 day in the absence of rIL-4. Following restimulation, secreted Th1 cytokines were quantitated. Bars represent means +/− S.E. where n=4. FIG. 3D, Secreted Th2 cytokines were quantitated after exposure to exogenous IL-4 according to the stimulation protocol described in FIG. 3C.

FIG. 4A, Acutely stimulated T cells from Camk4−/− mice do not produce IL-4 mRNA. Splenocytes were stimulated with plate-bound CD3 and CD28 antibodies for the indicated times. Total RNA was then isolated and analyzed for cytokine mRNA levels by RNase protection. n=4. FIG. 4B, CaMKIV activates the IL-4 gene promoter in Jurkat T cells. Jurkat cells were transiently transfected with an IL-4 luciferase reporter and expression plasmids for CaMKIV and CaMKK. Luciferase activity was determined from transfected cells which were either unstimulated or stimulated for 8 h with 0.5 μM ionomycin. Bars represent means +/− S.E. where n=3.

FIG. 5A, Secreted cytokines from CD4+ memory T cells. Following 3 days of stimulation with plate-bound CD3 and CD28 antibodies, the levels of IFN-γ, IL-4, and IL-5 secreted from memory cells were quantitated. Bars represent means +/− S.E. where n=5. FIG. 5B, Secreted cytokines from naïve T cells. Following 5 days of stimulation with plate-bound CD3 and CD28 antibodies, naïve cells were collected, washed, and restimulated for 1 day, at the end of which period secreted IFN-γ and IL-A were quantitated. Bars represent means +/− S.E. where n=3. FIG. 5C, Secreted cytokines from naïve T cells after exposure to exogenous IL-4. Naïve T cells were stimulated with CD3 and CD28 antibodies in the presence of exogenously added recombinant IL-4 (50 ng/ml). At the end of 5 days, the cells were collected, washed, and restimulated for 1 day in the absence of rIL-4. Following restimulation, secreted IFN-γ and IL-4 was quantitated. Bars represent means +/− S.E. where n=3. FIG. 5D, Secreted cytokines from naïve T cells after repetitive stimulation protocol. Naïve T cells were stimulated by plate-bound CD3 and CD28 antibodies in the presence of recombinant IL-2 (10 U/ml). Every two days the cells were collected, washed and restimulated with plate-bound antibodies in the presence of rIL-2. On day six, secreted IFN-γ, IL-4, and IL-5 were quantitated. Bars represent means +/− S.E. where n=3.

DETAILED DESCRIPTION OF THE INVENTION

Figure 1:
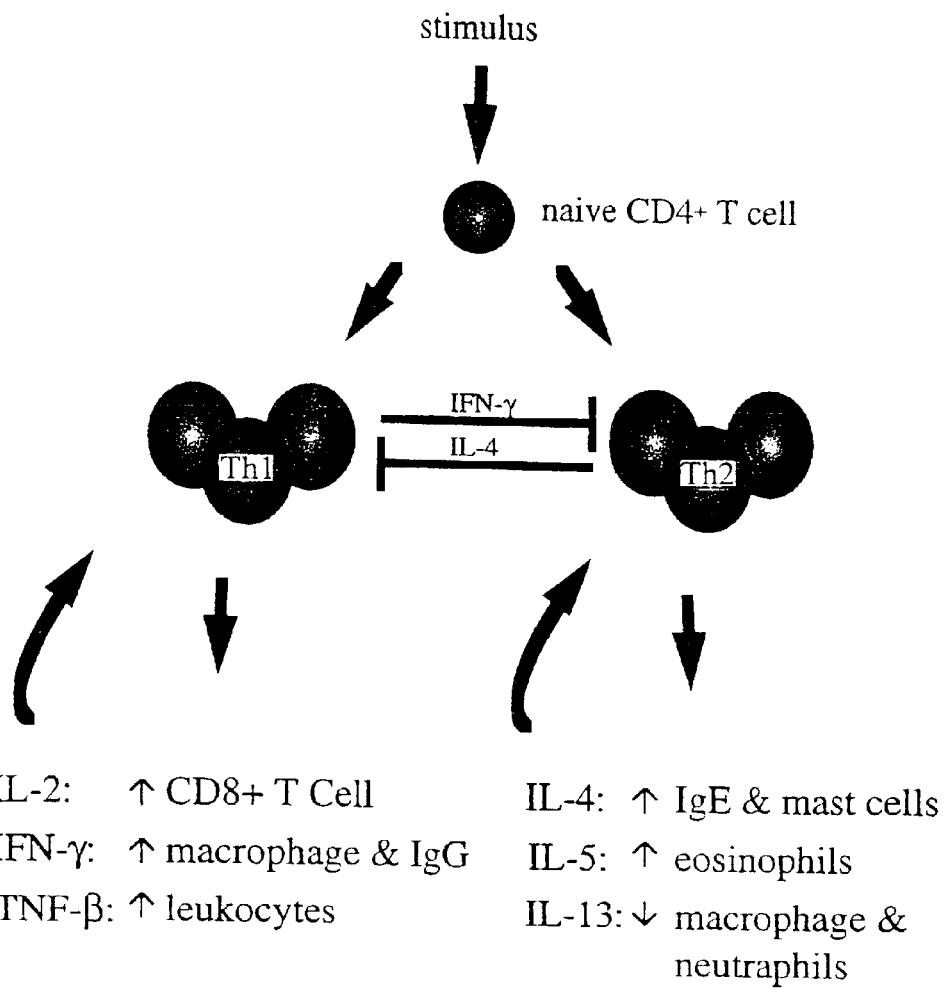
FIG. 1. CD4+ Th1 and Th2 subsets mediate different effector functions.

The present invention relates generally to agonists and antagonists of CaMKIV, and to methods of identifying same. The data presented herein establish that CaMKIV plays a role in immune responses and hematopoietic cell differentiation. The restricted tissue distribution of CaMKIV makes it an ideal therapeutic target for both stimulatory and inhibitory therapeutic agents as the toxicity of non-target tissues can be expected to be negligible.

The present invention thus relates, in one embodiment, to methods of screening compounds for their ability to act as CaMKIV agonists or antagonists. In this embodiment, the method comprises:

i) contacting CaMKIV and a substrate therefor, in the presence and absence of a test compound, under conditions such that CaMKIV-dependent phosphorylation of the substrate can be effected, and ii) determining, directly or indirectly, the level of phosphorylation of the substrate, wherein a reduction in phosphorylation of the substrate in the presence of the test compound is indicative of a CaMKIV antagonist (for example, an immunosuppressive agent) and an increase in phosphorylation of the substrate in the presence of the test compound is indicative of a CaMKIV agonist (for example, an immunostimulatory agent or a cell differentiation enhancing agent).

The method of the invention can be carried out in a cell free system or using cells in culture. Advantageously, a test compound is screened first in a cell free system and subsequently in an intact cell system. Cell free systems can include, in addition to CaMKIV and substrate, CaMKIV kinase, calmodulin and calcium, as well as a phosphate donor. The concentrations of the various system components can vary, however, one skilled in the art can readily optimize reaction as a matter of routine. The reaction can be carried out in a standard kinase buffer.

The substrate used in the cell free system is advantageously a peptide substrate. While CREB can be used, alternative substrates, such as syntide-2 from Bachem, can also be employed. Phosphate donors suitable for use in the present invention include ATP, a radiolabeled form, such as [γ-$^{32}$P]ATP, being preferred.

The effect of the test compound on the CaMKIV-dependent phosphorylation can be determined using a variety of approaches well known in the art. When $^{32}$P-ATP is used as the phosphate donor, the extent of phosphorylation of the substrate can be determined by monitoring the amount of $^{32}$P associated with the substrate.

In one specific embodiment of the above-described method, a test compound can be tested for its ability to competitively inhibit CaMKIV phosphorylation of a peptide substrate (e.g., GS10); standard protein kinase assays can be used (see generally Selbert et al, J. Biol. Chem. 270:17616 (1995)). For example, a reaction mixture comprising the test compound, the peptide substrate, CaMKIV, calcium, calmodulin, CaMKIV kinase and phosphate donor (e.g., bearing a detectable label, such as a radioactive label) is prepared and incubated under conditions such that the kinases present in the mixture can effect phosphorylation of their respective substrates (a constitutively activated form of CaMKIV can be used in the reaction mixture in lieu of CaMKIV, in which case the CaMKIV-activating components (e.g., CaMKIV kinase) need not be present). The reaction mixture is then processed so as to eliminate labeled phosphate not associated with substrate (i.e., non-incorporated labeled phosphate). For example, the reaction mixture can be applied to an ion exchanger, for example, an ion exchange filter (e.g., a P81 filter). The ion exchanger (e.g., filter) is then washed and the amount of detectable label associated therewith determined and compared with the amount of detectable label associated with a control ion exchanger (i.e., an ion exchanger to which a reaction mixture as described above but minus test compound, is applied). A reduction in the amount of detectable label associated with the ion exchanger (and thus with substrate) in the presence of the test compound (relative to the control) is indicative of a CaMKIV antagonist.

CaMKIV must bind Ca$^{2+}$/calmodulin to be active. Further, CaMKIV must be phosphorylated on Thr-200 (in the human form of the enzyme) by CaMKIV kinase. This phosphorylation can be readily detected, for example, by separating the components of the reaction mixture (as described above), for example, on a polyacrylamide gel, and quantifying the amount of detectable label incorporated into CaMKIV, for example, by phosphoimaging. Since phosphorylation of CaMKIV is required for CaMKIV activation, a test compound that inhibits or enhances CaMKIV kinase can also be expected to be, for example, an effective immunomodulatory agent or agent that modulates cell differentiation. The effect of a test compound on the phosphorylation events (e.g., phosphorylation of CaMKIV by CaMKIV kinase or phosphorylation of CaMKIV substrate by CaMKIV) can be measured in a single reaction. To effect this simultaneous screen, Ca$^{2+}$/calmodulin, CaMKIV kinase, CamKIV, substrate for CaMKIV and labeled phosphate donor (e.g., $^{32}$P ATP) can be combined with a standard protein kinase assay reaction mixture. After incubation, an aliquot of the resulting reaction mixture is applied, for example, to a P81 filter and processed as described above for determination of CaMKIV substrate phosphorylation. This provides an assessment of CaMKIV activity. A further aliquot is, for example, run on a polyacrylamide gel and the amount of labeled phosphate incorporated into the CaMKIV quantified, for example, by phosphoimaging. This provides an assessment of CaMKIV kinase activity. CaMKIV is the only known substrate of the CaMKIV kinase, except for CaMKI. At present, CaMKI does not have a known physiological function. (See generally assay details provided in Selbert et al, J. Biol. Chem. 270:17616 (1995)).

As indicated above, test compounds screened in the cell free system can also be screened using a system based on cells in culture. Cells that contain CREB and CaMKIV naturally (e.g., T cells) can be used in such screens, as can cells resulting from engineering. Mammalian as well as non-mammalian engineered cells can be used, lymphocytes or fibroblasts transfected with a CaMKIV encoding sequence being examples, as are yeast cells transfected with sequences encoding the required proteins. (See Sun et al, Genes & Develop. 8:2527 (1994).) Cells can be stimulated using a variety of approaches, including use of a calcium ionophore or occupancy of the T cell receptor. As in the case of the cell free system, the immunomodulatory activity of a test compound can be determined by assessing the extent to which the substrate (e.g., CREB) is phosphorylated. While a variety of techniques can be used (including quantitating the transfer of $^{32}P$ from a radiolabeled phosphate donor to the substrate), the use of antibodies specific for the phosphorylated form of the substrate (e.g., antibodies specific for the phosphorylated form of CREB) is preferred.

Compounds demonstrated to have activity as a CaMKIV agonist or antagonist based on one or more of the above-described screens can be modified as appropriate to minimize toxic effects and the like. Where T cell specificity is desired, compounds identified in accordance with the present methods can also be derivatized, if necessary, to ensure that they do not cross the blood brain/testis barrier.

Screening procedures such as those described above are useful for identifying agents for their potential use in pharmacological intervention strategies. The Th1/Th2 balance during immune responses can profoundly affect the outcome of such responses. Therefore, a specific molecule that influences this balance, such as CaMKIV, is an ideal target for a broad array of therapies. Prevention of allergic asthma is one such example. Both IL-4 and IL-13 are known to contribute to this disease. Th2 cells required IL-4 to differentiate and then produce IL-4 and IL-13. By preventing formation of Th2 cells, a CaMKIV antagonist idenfiable using the present methods of screening can be expected to prevent development of allergic asthma. CaMKIV antagonists can be used to arrest the persistence and progression of any of a variety of chronic inflammatory diseases. Specific examples of areas in which agents identified as being CaMKIV antagonists find applicability include treatment of autoimmune diseases, including multiple sclerosis, rheumatoid arthritis, and systemic lupus erythematosis, and treatment of patients undergoing organ and tissue (including bone marrow) transplantation. Vasculitis, arthritis and nephritis, either secondary to the deposition of immuno-complexes (like in post-streptococcal glomerulonephritis) or to the presence of autoantibodies (like in Goodpasture syndrome and all vasculitis due to circulating Antibodies against Neutrophil Cytoplasmic Agents, ANCA), all involve the inappropriate activation of the complement cascade and of neutrophils. Immunosuppressant drugs more specific than corticosteroids avoid many of the undesired side effects so prevalent in steroid therapy.

The involvement of CaMKIV in hematopoietic differentiation, demonstrated by studies described herein, indicate that CaMKIV activators (e.g., those identifiable using the present screening methods) can be used to treat diseases featuring differentiation defects, such as the aplastic anemias, both idiopathic and secondary to antiblastic therapy. In the latter case, the use of a CaMKIV agonist can be expected to allow better recovery in between chemotherapeutic cycles.

The present invention also relates to pharmaceutical compositions comprising, as active agent, compounds selected using one or more of the above-described screening protocols. Such compositions include the active agent(s) in combination with a pharmaceutically acceptable carrier. The amount of active agent in the composition can vary with the agent, the patient and the effect sought. Likewise, the dosing regimen, including mode of administration, will vary depending on the composition and the disease/disorder to be treated.

Studies described herein demonstrate that CaMKIV plays multiple roles in hematopoiesis in the bone marrow. CaMKIV is localized on the long arm of human chromosome 5 in a cluster of genes known to be important for hematopoiesis. These genes include GM-CSF, M-CSF, c-fms, IL-4, IL-5 and EGR-1. This area on chromosome 5 is known to be involved in the 5q-myelodysplastic syndrome, therapy-related myelodysplastic syndrome and acute leukemias. Such diseases often feature interstitial deletions of this 5q cluster. Thus, CaMKIV may be a predisposing factor for this series of human diseases.

The studies described in Example 3 demonstrate that, in the absence of CaMKIV, stimulated CD4+ memory phenotype T cells are unable to produce cytokines. The number of cells recovered from the CaMKIV−/− mice and the distribution of surface markers indicative of the memory cell phenotype are normal, indicating that the development and survival of this population has not been compromised. However when stimulated, the mutant cells fail to phosphorylate CREB and fail to induce the CREB-dependent IEGs required for cytokine gene induction. These findings indicate that CaMKIV is required for CREB phosphorylation during memory phenotype CD4+ T cell activation and, when absent, creates an acute signaling defect responsible for diminished cytokine production. Stimulated naïve T cells from CaMKIV−/− mice, in contrast, do not have an apparent problem producing cytokines. The results raise the question as to why CaMKIV is needed for CREB phosphorylation in one, but not the other cell type. While not wishing to be bound by theory, it is possible that it may have to do with features that are distinct between naïve and memory cells (Abbas et al, Nature 383:787 (1996), Dutton et al, Annu. Rev. Immunol. 16:201 (1998)). Naïve T cells are mature cells that have never been activated. Once activated by the appropriate antigen, in the presence of additional co-stimulatory and cytokine signals, the cells are driven to differentiate into cytokine producing effector cells. As antigen is eliminated, the majority of effectors die, but some further differentiate into long-lived memory cells. Memory cells differ from naïve cells most clearly with respect to function. When activated, memory T cells immediately secrete large quantities of cytokines, without having to go through the process of differentiation. In addition their requirements for activation, such as antigen dose and co-stimulation, that leads to proliferation and cytokine production are not as strict. It may be that signals proximal to the TCR are differentially coupled to downstream events in naïve and memory cells. The results presented in Example 3 indicate that the regulation of CREB phosphorylation is a specific point of divergence between naïve and memory cell signaling. One way that CREB phosphorylation may be differentially regulated in naïve and memory cells is through differential dependence on RSK2 and CaMKIV pathways in the two cell types. It has been demonstrated that the MAP kinase RSK2 is expressed at the same level in naïve and memory phenotype cells and that it can be upshifted to the activated form to similar extents when the cells are stimulated. Therefore, dominance of a CaMKIV pathway in memory phenotype cells cannot be attributed simply to the absence of an RSK2 pathway. CaMKIV in some instances can stimulate MAPK pathways. However, RSK2 expression and activation are unperturbed in memory phenotype cells from CaMKIV−/− mice. It is also possible that CaMIV-dependent CREB phosphorylation is important in both naïve and memory cells, but that naïve cells are specifically able to compensate in the absence of the kinase. In this regard, it is relevant that thymocytes, which express high levels of CaMKIV, exhibit no obvious developmental or functional defect. They too, may be able to compensate for the absence of the kinase. Because of their unique functional properties, memory T cells are able to mediate long-term protective immunity by providing the animal with an accelerated immune response upon reexposure to antigen, critical in controlling infection and preventing disease. The studies in Example 3 define an important signaling role for CaMKIV in this critical T cell subtype.

Certain aspects of the present invention are described in greater detail in the non-limiting Examples that follow.

EXAMPLE 1

Defective Differentiation of CD4+ T Cells to T Helper Type 2 Cells in the Absence of $Ca^{2+}$/Calmodulin-Dependent Protein Kinase IV Experimental Details CaMKIV−/− Mice The generation of Camk4−/− mice by targeted gene disruption in embryonic stem cells has been previously described (Park et al, J. Biol. Chem. 270:30464 (1995)). The mutation was maintained on a mixed 129/Sv×C56BL/J6 genetic background. For the experiments described, mice 3–6 weeks of age were sacrificed.

Cell Preparation and Surface Staining

Cells from spleen and inguinal lymph node were cultured in RPMI-1640 growth media supplemented with 10% heat inactivated fetal bovine serum (Gibco BRL, lot 1019504), 100 U/ml penicillin, 100 µg/ml streptomycin, and 50 µM 2-mercaptoethanol. Enrichment of CD4+ single positive T cells from lymph node and spleen was achieved by negative selection using mouse CD8 and B220 magnetic beads (Dynal, Lake Success, N.Y.). Purity of the resulting populations assessed by fluorescence-activated cell sorter (FACS) analysis was >90%. For some experiments, CD4+ single positive T cells were separated into naïve and memory T cells. This was achieved by double staining the cells with antibodies against L-selectin and NK1.1 followed by sorting with a Becton-Dickinson FACS into L-selectin$^{hi}$/NK1.1 negative (naïve T cells) and L-selectin$^{lo}$/NK1.1 negative (memory T cells) populations. The total number of viable cells was determined by trypan blue exclusion.

In vitro Cytokine Production

CD4+ T cells were stimulated at a density of 0.25×10$^6$ cells per ml with plate-bound CD3 (clone 145-2C11, Pharmingen) and CD28 (clone 37.51, Pharmingen) antibodies, each at 5 µg/ml. After 5 days of culture, the cells were pelleted, washed, counted by trypan blue exclusion, and restimulated by plate-bound CD3 and CD28 antibodies for one additional day. Where indicated, exogenously added recombinant IL-4 (Sigma, I1020) was included during stimulation at 50 ng/ml. Following restimulation, growth media was assayed for secreted cytokines according to the Pharmingen cytokine sandwich ELISA protocol. The repetitive stimulation protocol consisted of stimulating the cells with plate-bound anti-CD3 and anti-CD28 as described above, but in the presence of recombinant IL-2 (Pharmingen, 19211T) at 100 ng/ml. Every two days the cells were pelleted, washed, and restimulated with plate-bound antibodies.

In vitro T Cell Proliferation

CD4+ T cells were stimulated with plate-bound CD3 and CD28 antibodies (each at 5 µg/ml) for 3 days at a density of 0.25×10$^6$ cells/ml. [3H]Thymidine was included during the last 6 h of culture. Cells were lysed by adding ½ volume of 50% TCA and incubating 10 min at room temperature. Precipitated DNA was collected on glass fiber filters (#31, Whatman), and incorporated [3H]thymidine quantitated by scintillation counting.

Transient Transfections

TAg Jurkat cells were maintained in RPMI medium supplemented with 10% fetal bovine serum. Cells at log growth phase were transfected by electroporation at 250 V and 960 microfarads with 3 µg of luciferase IL-4 promoter reporter and pSG5 expression plasmid (Stratagene) containing CaMKIV (3 µg) or CaMKKB (3 µg), as indicated. Luciferase activity was determined using beetle luciferin (Promega) according to the manufacturer.

RNase Protection

Total RNA was isolated from splenocytes using ultraspec RNA (Biotecx) after acute stimulation of the cells with plate-bound anti-CD3 and anti-CD28 antibodies. RNase protection was carried out using the RiboQuant Rnase protection assay system (Pharmingen) with the mCK-1 multi-probe template set (Pharmingen). Riboprobe labeling was with [a-$^{32}$P]UTP.

Immunoglobulin Quantitation

Immunoglobulin levels in serum were quantitated using antibodies from Pharmingen and the sandwich ELISA protocol recommended by the manufacturer.

Results

Figure 2A:
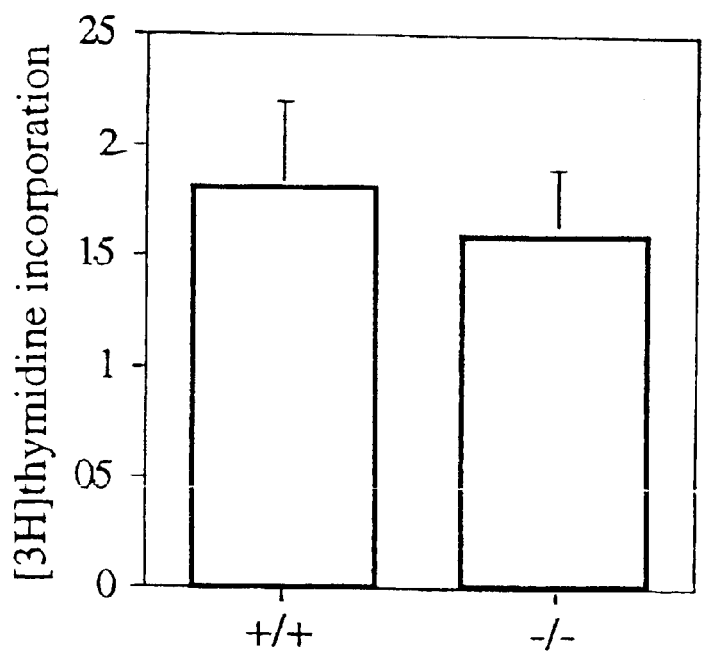
FIGS. 2A and 2B. CD4+ T cells from Camk4−/− mice proliferate normally in response to TCR ligation, FIG. 2A, CD4+ T cells were pulsed for 6 h with [3H]thymidine following 2.5 days of stimulation with plate-bound CD3 and CD28 antibodies. Bars represent means +/− S.E. where n=4.
Figure 2B:
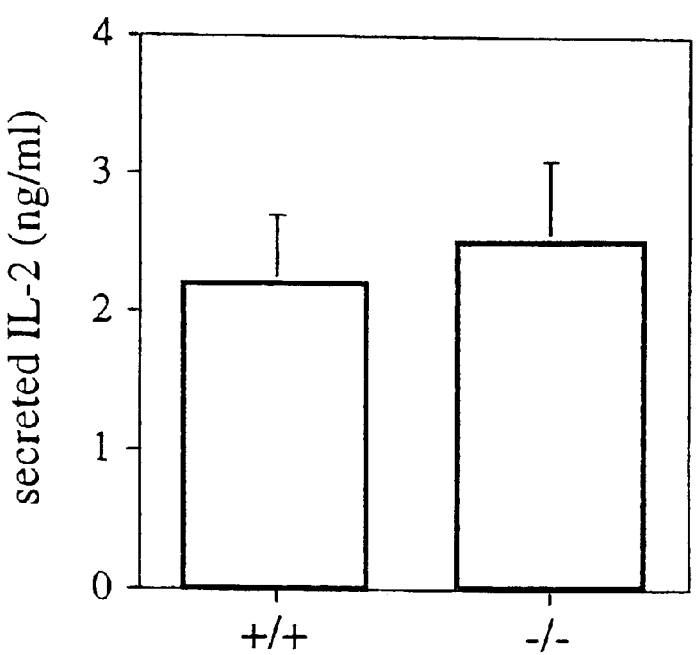

A CaMKIV-deficient mouse previously generated by targeted gene disruption in murine embryonic stem cells was used to address the role of CaMKIV in CD4+ T cell differentiation. CD4+ T cells isolated from the lymph nodes of Camk4−/− or wild type mice and stimulated with CD3 and CD28 antibodies produce similar proliferative responses (FIG. 2A). Consistent with normal proliferation, stimulated CD4+ T cells from Camk4−/− mice produce normal levels of IL-2, the major T cell growth factor (FIG. 2B).

Figure 3A:
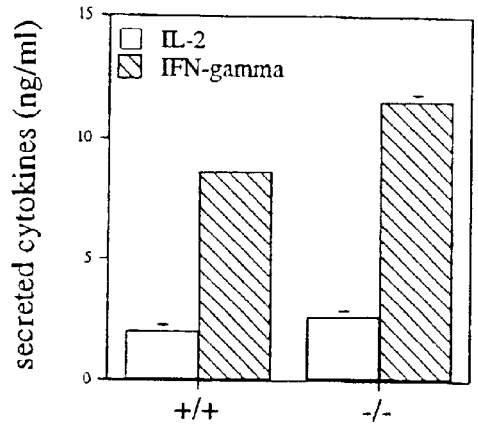
FIGS. 3A–3D. CD4+ T cells from Camk4−/− mice display a defective Th2 response which can be restored by exogenous IL-4.
Figure 3B:
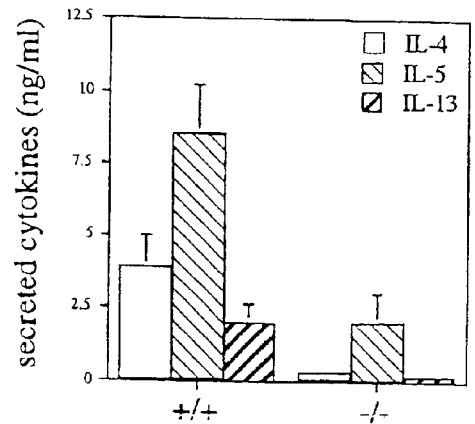

To determine whether CaMKIV plays a role in helper T cell differentiation, CD4+ T cells from Camk4−/− and wild type mice were stimulated continuously with CD3 and CD28 antibodies for a five day priming period, during which time differentiation into effector cells occurs. The cells were washed, counted, and equal numbers restimulated overnight with CD3 and CD28 antibodies. Quantitation of cytokines secreted during the overnight restimulation is shown in FIG. 3. CD4+ T cells from Camk4−/− and wild type mice produce similar levels of IFN-γ, the major Th1 cytokine, indicating that Th1 differentiation occurs in the mutant (FIG. 3A). In sharp contrast, T cells from the Camk4−/− mice produced 10 fold less IL-4, the major Th2 cytokine, compared to wild type cells (FIG. 3B). The levels of two other Th2 cytokines, IL-5 and IL-13, were also severely reduced, indicating a profound block in Th2 differentiation.

Figure 3C:
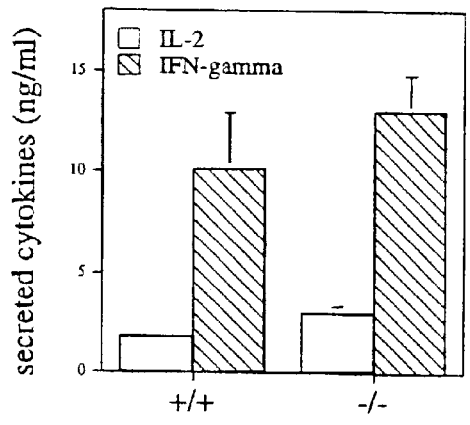
Figure 3D:
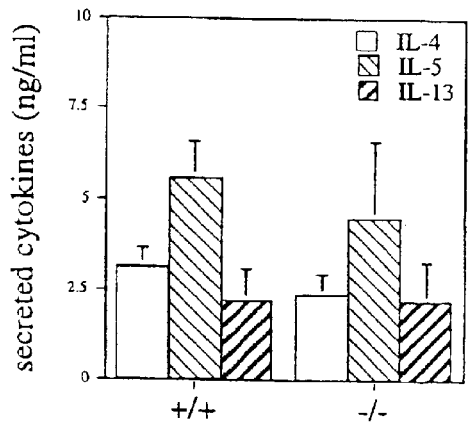
Figure 4A:
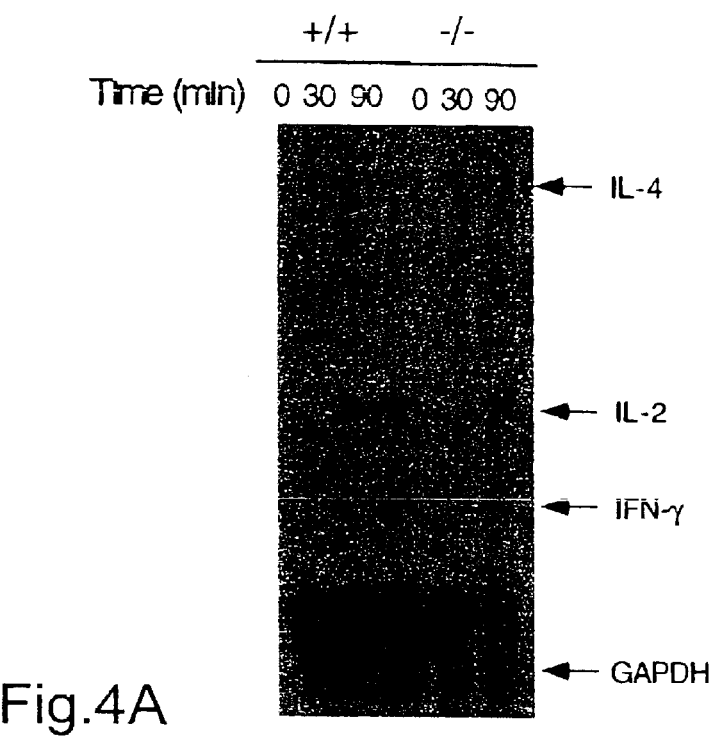
FIGS. 4A and 4B. Activation of the IL-4 gene by CaM KIV.
Figure 4B:
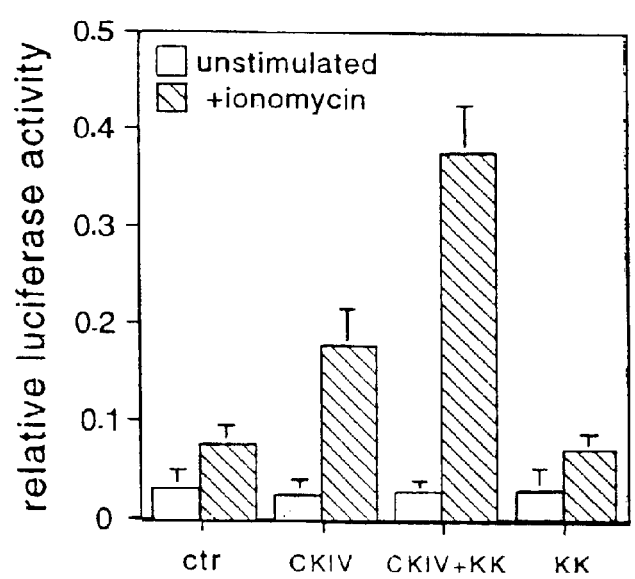

Since IL-4 is required for Th2 differentiation, a determination was made as to whether the lack of Th2 response in the mutant T cells was a direct result of their inability to make IL-4. As shown in FIG. 3D, addition of exogenous IL-4 during the priming period completely restored secretion of IL-4, IL-5, and IL-13 by the mutant cells, but had no effect on the levels of secreted IL-2 or IFN-γ (FIG. 3C). This suggested that the defect observed results from an inability of the Camk4−/− CD4+ T cells to generate the early IL-4 signal required for the initiation of Th2 differentiation. To test this possibility, IL-4 gene induction following acute stimulation of the-cells was examined. RNase protection demonstrated that T cells from Camk4−/− mice are unable to transcribe the IL-4 gene, although IL-2 and IFN-γ transcription appear normal (FIG. 4A). This raised the possibility that CaMKIV may be required for induction of the IL-4 gene. To determine whether CaMKIV is capable of activating the IL-A promoter, Jurkat cells were transiently transfected with an IL-4 promoter luciferase reporter. Luciferase activity was increased 2 fold in cells cotransfected with CaMKIV expression plasmid and stimulated with ionomycin (FIG. 4B). The stimulation was further increased to 5 fold when the upstream CaMkinase kinase (CaMKK) was included in the co-transfection. This demonstrates that CaMKIV is able, in the presence of a $Ca^{2+}$ signal, to activate the IL-4 promoter in a T cell line.

Figure 5A:
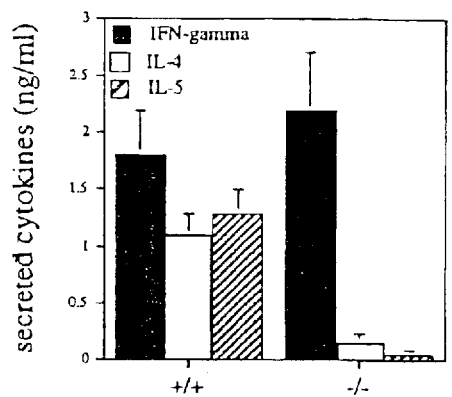
FIGS. 5A–5D. Naïve and memory CD4+ T cells from Camk4−/− mice display a defective Th2 response. CD4+ T cells were sorted into L-selectin$^{hi}$ (naïve T cells) and L-selectin$^{low}$ (memory T cells) populations.
Figure 5B:
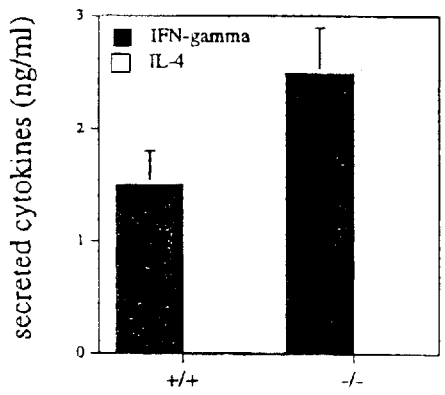
Figure 5C:
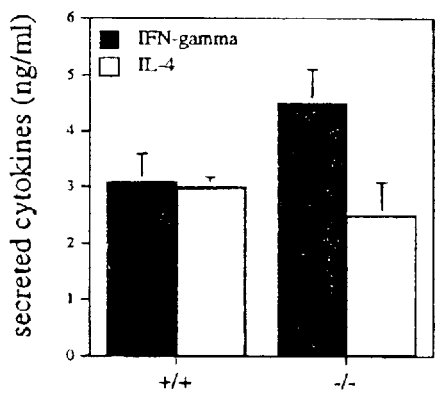

The CD4+-enriched population of T cells used in the previous experiments was comprised of naïve and memory cells, both of which are capable of producing IL-4. To determine more precisely the cell type which is defective in the Camk4−/− mice, CD4+ cells were sorted into naïve and memory populations based on L-selectin surface expression (Bradley et al, J. Immunol. 148:324–331 (1992)). The L-selectin staining profiles of wild type and mutant cells appear similar to previously reported patterns, with approximately 75% staining L-selectin$^{high}$ (naïve T cells) and 25% staining L-selectin$^{low}$ (memory T cells) (Lee et al, J. Immunol. 144:3288–3295 (1990)). When stimulated with CD3 and CD28 antibodies, memory T cells from wild type animals secreted large amounts of IFN-γ, IL-4 and IL-5. In contrast, memory cells from Camk4−/− mice secreted normal levels of IFN-γ, but severely reduced amounts of IL-4 and IL-5, demonstrating that the Th2-polarized memory compartment is defective or absent in the Camk4−/− mice (FIG. 5A). When naïve T cells were assayed for cytokine production, both wild type and mutant cells produced IFN-γ, but no detectable IL-4 unless exogenous IL-4 was included during stimulation (FIGS. 5B,C). This result demonstrates that with a single stimulation, naïve cells do not support their own Th2 differentiation.

Figure 5D:
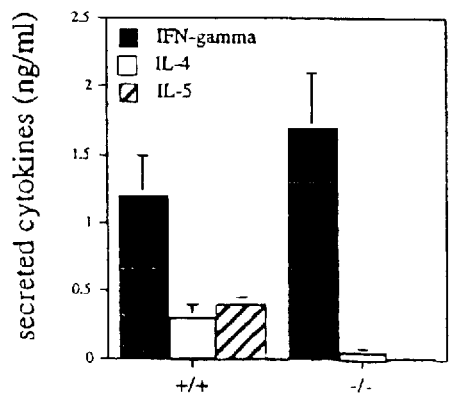

Recently activated naïve CD4+ T cells require repetitive stimulation in order to produce sufficient autocrine IL-4 to support Th2 differentiation (Croft et al, J. Immunol. 154:4269–4282 (1995), Demeure et al, Eur. J. Immunol. 25:2722–2725 (1995)). Using a repetitive stimulation protocol, Camk4−/− naïve CD4+ T cells were tested for their ability to secrete IL-4 and differentiate along a Th2 pathway. Naïve cells from wild type mice secreted IFN-γ, IL-4, and IL-5. However, whereas cells from Camk4−/− mice produced similar amounts of IFN-γ, production of IL-4 and IL-5 was significantly attenuated (FIG. 5D). This indicates that naïve CD4+ T cells from Camk4−/− mice are unable to produce sufficient autocrine IL-4 to support Th2 differentiation. Two major physiological consequences of a Th2 response are the induction of B cell production of the immunoglobulin, IgE, and the activation and amplification of eosinophils (Abbas et al, Cell 100:129–138 (2000); Abbas, Nature 383:787–793 (1996)). Three representative Camk4 mice were found to exhibit an approximately 10 fold lower serum IgE level compared to control animals, while levels of the Th1-dependent isotype IgG2a, were unaffected (see Table 1). In addition, the number of circulating eosinophils was significantly reduced in Camk4−/− mice compared to control animals. These results indicate that the physiological Th2 response is impaired in Camk4−/− mice.

EXAMPLE 2

Figure 6:
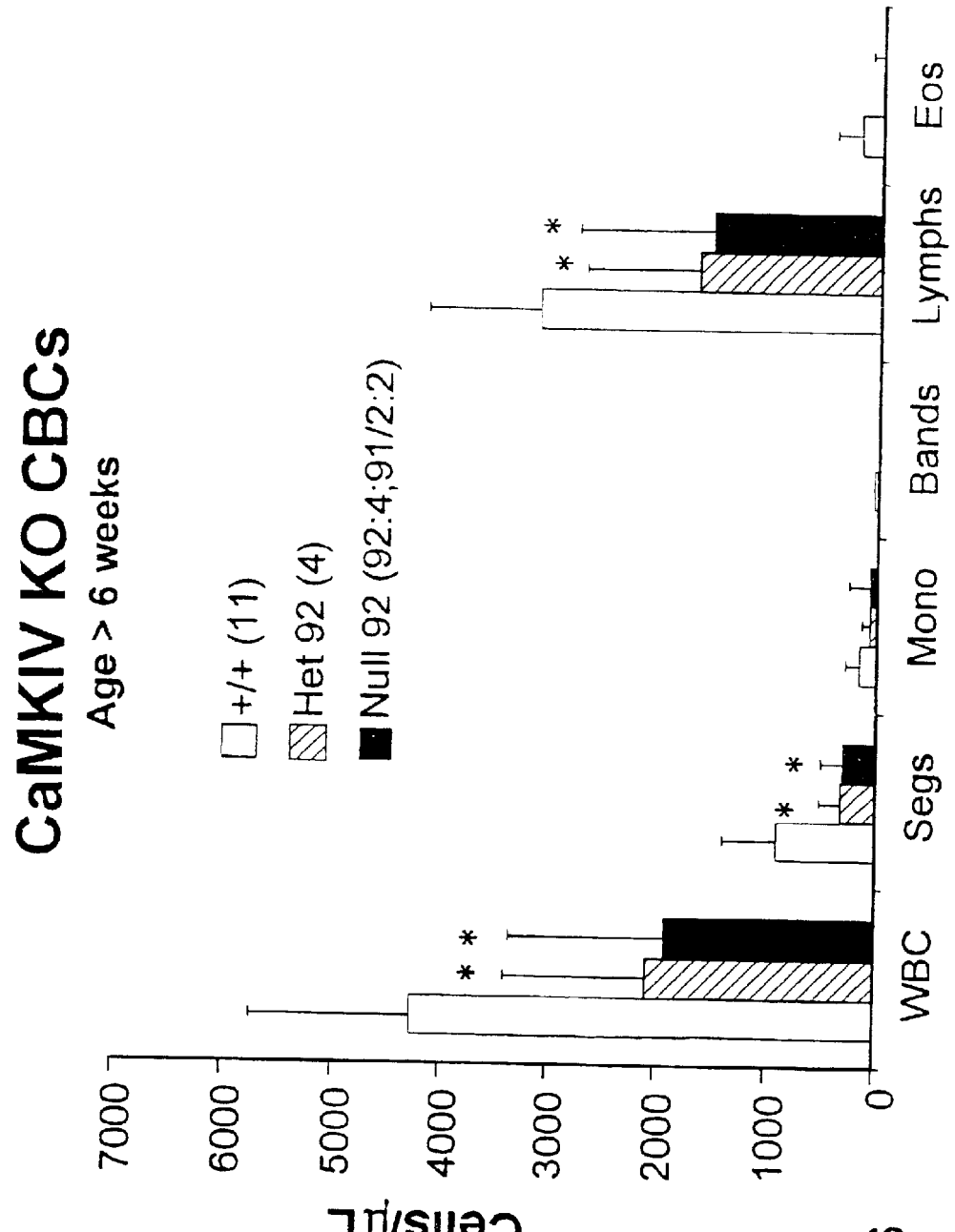
FIG. 6. Peripheral blood cell counts of wild type (+/+), heterozygous (+/−), null (−/−) mice. Numbers are expressed in cells/μL. The White Blood Cell (WBC) differential (Segs=segmented cells; Lymps=lymphocytes) was evaluated morphologically on blood smears on 100 cell count. Asterisk represents p<0.05 (unpaired t-test) versus wild type.

As a component of the phenotypic analysis of the CaMKIV null mice (Camk4−/−), the distribution of hematopoietic cells in the blood was examined. Surprisingly, the mice exhibited profound leukopenia characterized by a marked decrease in both neutrophils and lympocytes (FIG. 6). A determination was made as to whether CaMKIV was expressed in the bone marrow (BM) and, if so, whether BM defects existed in the Camk4−/− mice. Indeed, immunocytochemical and biochemical analysis revealed that CaMKIV is present in both human and mouse bone marrow cells. Expression occurs in early hematopoietic progenitors (Lyn−), as well as cells in the myeloid lineage including neutrophils and macrophages.

Figure 7:
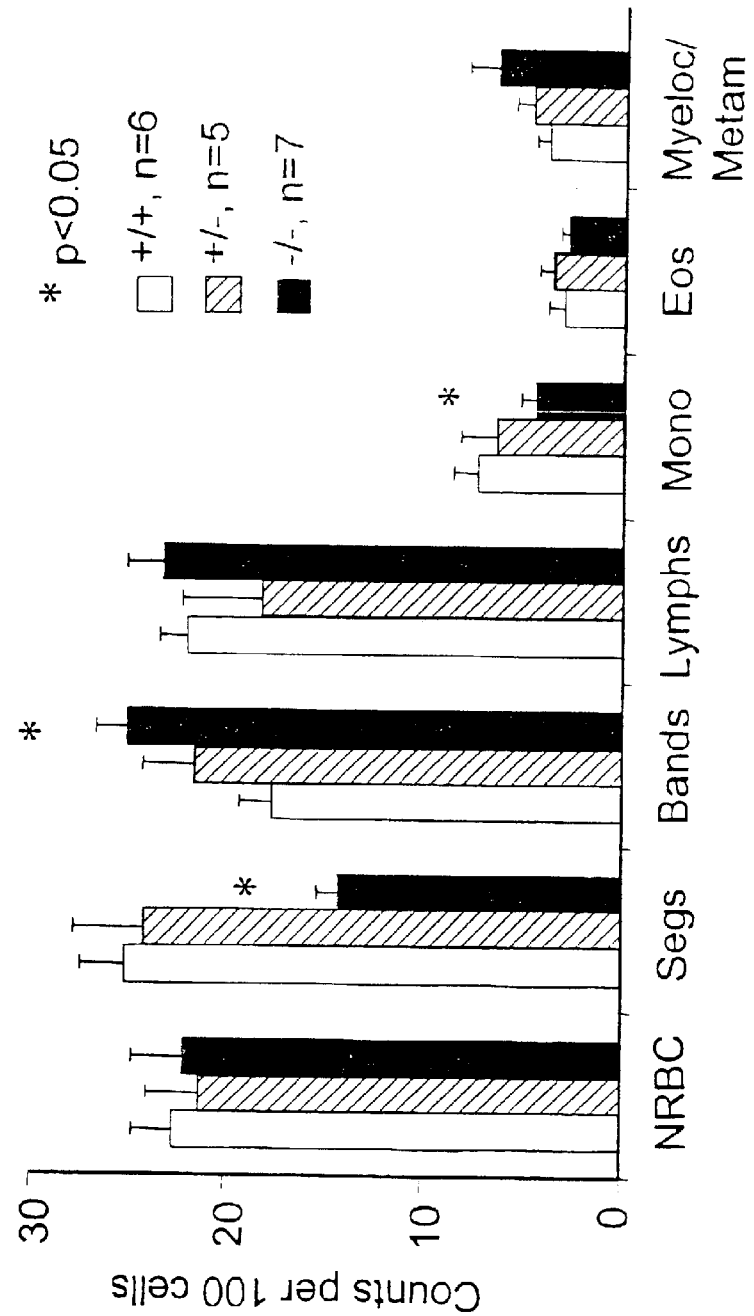
FIG. 7. Differential cell type counts were performed on BM cytospins of wild type (+/+) heterozygous (+/−) and null (−/−) mice on 200 cell count. Asterisk represents p<0.05 (unpaired t-test) versus wild type.

To address the consequences of the delection of the CaMKIV gene on hematopoiesis, cytomorphology was used to evaluate the BM as shown in FIG. 7. The results revealed a reduction of segmented cells (Segs) coupled with a concomitant increase of banded cells (Bands) which are the immediate precursors of the Segs. Monocytes are also decreased indicating a defect in the entire myeloid lineage. Finally, whereas neutrophils are present in the BM, they contain large vacuoles in the cytoplasm and this is also an a typical phenotype.

Figure 8:
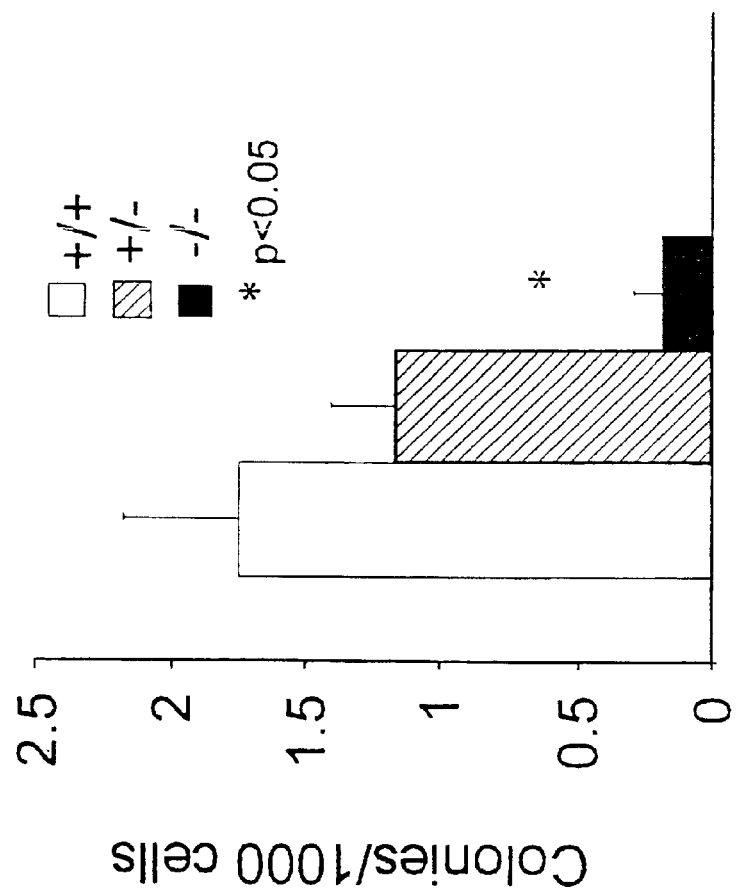
FIG. 8. Unfractionated BM cells were plated on methylcellulose medium complete with hematopoietic growth factors, including erythropoietin. At 5 weeks of culture the number of colonies was counted. Each sample was plated in quadruplicate. Asterisk represents p<0.05 (unpaired t-test) versus wild type.

Because CaMKIV was present in early hematopoietic precursors, the ability of unfractionated BM of the Camk4−/− mice to form colonies in methylcellulose was examined. FIG. 8 shows a substantial reduction in colony formation indicating that a defect in committed progenitors occurs in the absence of CaMKIV. Together the data indicate that CaMKIV plays more than one key role in hematopoiesis in the BM.

Since CaMKIV was found to be present in neutrophils, a determination was made as to whether the enzyme was important for neutrophil function. In isolated peripheral neutrophils from normal mice or humans, the responses of neutrophils to stimulation by the chemotactic peptide, fMLP, or by the phorbol ester, PMA, was evaluated. Both the respiratory burst and hydrogen peroxide production were completely inhibited by addition of an antagonist known to inhibit CaMKIV, KN-93. It was known that the MPA kinase, p38, is required for the respiratory burst that follows neutrophil activation. KN-93 also prevented p38 activation in response to either fMLP or TPA. BM neutrophils have been isolated from normal and Camk4−/− mice and p38 activation in response to PMA has been evaluated. Whereas p38 is activated with 90 minutes in neutrophils from control mice, the Camk4−/− neutrophils failed to activate p38. These data indicate that CaMKIV is important for p38 phosphorylation and, thus, for neutrophil activation.

EXAMPLE 3

Defective Memory Phenotype CD4+ T Cell Function in the Absence of CaMKIV

Experimental Details

Mice. The CaMKIV−/− mice used in this study were maintained on a C57BL/cj129 mixed genetic background. Animals used were 5–10 weeks of age.

T cell isolation and stimulation. Enrichment of CD4+ single positive T cells from spleen was achieved by negative selection with mouse CD8 and B220 magnetic beads (Dynal, Lake Success, N.Y.). Purity of the resulting populations assessed by fluorescence-activated cell sorter (FACS) analysis was >90%. Initially, separation of CD4+ T cells into naïve and memory T cell populations was achieved by triple staining with antibodies against the NK1.1, L-selectin, and CD44 surface markers, followed by sorting by a Becton-Dickinson FACStar into NK1.1$^{negative}$/L-selectin$^{high}$/CD44$^{low}$ (naïve T cells) and NK1.1$^{negative}$/L-selectin$^{low}$/CD44$^{high}$ (memory phenotype T cells) populations (Bradley et al, J. Immunol. 148:324 (1992), Budd et al, J. Immunol. 138:3120 (1987)). It was subsequently discovered that the sorted cells behaved similarly whether NK1.1 was selected against or not. For this reason some separations were made based only on L-selectin and CD44 surface marker expression. Similar experimental results were obtained when naïve and memory T cell separation was achieved by staining with antibodies against the CD45RB and CD44 surface markers followed by sorting into CD45RB$^{high}$/CD44$^{low}$ (naïve) and CD45RB$^{low}$/CD44$^{high}$ (memory) (Lee et al, J. Immunol. 144:3288 (1990)). The sorted cells were cultured in RPMI-1640 growth media supplemented with 10% heat inactivated fetal bovine serum (Gibco BRL, lot 1019504), 100 U/ml penicillin, 100 μg/ml streptomycin, and 50 μM 2-mercaptoethanol. The cells were stimulated at a density of 0.25×10$^6$/ml for the indicated times in 96-well plates which had been coated with 100 μl of CD3 (clone 145-2C11, Pharmingen) and CD28 (clone 37.51, Pharmingen) antibody, each at 5 μg/ml. To promote Th1 or Th2 differentiation of naïve CD4+ T cells, cells were primed for 4 days in standard growth media supplemented with recombinant IL-12 (2 ng/ml) and with IL-4 neutralizing antibody (10 μg/ml) or with recombinant IL-4 (50 ng/mL), respectively. Restimulation consisted of pelleting, washing, counting by trypan blue exclusion, and reculturing the cells with plate-bound CD3 and CD28 antibodies for one additional day.

T cell proliferation and survival assays. T cell proliferation was indirectly determined by measuring [3H]thymidine incorporation. CD4+ T cells, cultured in 96-well plates (0.25×10$^6$ cells/ml), received 1 μCi [3H]thymidine/well during the last 6 h of either 45 h or 72 h incubations. Incorporated radioactivity was determined by liquid scintillation counting. Cell survival was determined by incubating an aliquot of cells in 10% trypan blue dye for 5 min at room temperature. Living cells, which exclude dye, were counted on a hemocytometer.

Secreted cytokine determination. Growth media was assayed for secreted cytokines according to the PharMingen cytokine sandwich ELISA protocol using anti-mouse monoclonal capture and biotin-conjugated detection antibody pairs from PharMingen. Recombinant IL-2, IL-4, and IFN-γ protein from PharMingen was used to generate standard curves.

Competitive RT-PCR. Total RNA was isolated from 1–2× 10$^5$ naïve or memory CD4+ T cells using ultraspec RNA reagent (Biotecx). First strand cDNA was then generated using the ProSTAR first-strand RT-PCR kit (Stratagene) with Moloney murine leukemia virus reverse transcriptase (MMLV-RT) and random primers. Competitive RT-PCR has been described in detail (Reiner et al, J. Immunol. Meth. 165:37 (1993)). Briefly, RT reaction mixtures were standardized for total cDNA levels by assaying aliquots for HPTR cDNA by PCR in the presence of a series of HPRT competitor construct dilutions. After adjusting cDNA quantities to equivalent levels, cytokine transcript levels were semi-quantitated by PCR using cytokine specific primer pairs and competitor cDNA. The IL-2 primers, 5'CTGAAACTCCCCAGGATGCTC-3' (SEQ ID NO.8) and 3'-CTGTCAAAGTATCATCTAACAAGCC-5 (SEQ ID NO.9) amplified a 300 bp product, the IL-4 primers, 5'-ATCGGCATTTTGAACGAGGTC-3' (SEQ ID NO.10) and 3'-GAATGAGTCCAAGTCCACATCACTG-5' (SEQ ID NO.11) amplified a 272 bp product, the IFN-γ primers, 5'-AAAGGAGTCGCTGCTGATTCGG-3' (SEQ ID NO.12) and 3'-GAAAACTGTGACTACACCCGATGAC-3' (SEQ ID NO.13) amplified a 571 bp product and the HPRT primers 5'-GTTGGATACAGGCCAGACTTTGTTG-3' (SEQ ID NO.14) and 3'-CTCCCATCCGACCGGATATCCGA-5' (SEQ ID NO.15) amplified a 350 bp product. To create competitor constructs for HPRT, IL-2, IL-4, and IFN-γ, the wild type PCR products were subcloned into pCR2 (Invitrogen) and digested with a unique-site restriction endonuclease within the murine cDNA. Spacer DNA was generated by parallel digestion of mouse genomic DNA, which was then size fractionated by agarose gel electrophoresis. DNA pieces of convenient size were extracted from the gel and ligated into the digested recombinant plasmids to increase the size of the wild type genes. The HPRT PCR product was increased in size to ~1000 bp by an ~650 bp Hind3 fragment, the IL-2 PCR product was increased to ~650 bp by an ~350 bp Bgl2 fragment, the IL-4 PCR product was increased to ~750 bp by an ~750 bp EcoR1 fragment, and the IFN-γ PCR product was increased to ~900 bp by an ~351 bp fragment. The c-fos, Fra2, FosB, and junB transcript levels were determined by RT-PCR using specific primer pairs but without competitor constructs. The c-fos primers, 5'-TTTCCTACTACCATTCCCCA GCCG-3' (SEQ ID NO.16) and 3'-CTTGAAGATGAGAAGTCTGCGTTGC-5' (SEQ ID NO.1) amplified a 457 bp PCR product, the FosB primers, 5'-TGAGAGATTTGCCAGGGTCAAC-3' (SEQ ID NO.2) and 3'-GTGCTCCGTCTCTGGTTTTCTG-5' (SEQ ID NO.3) amplified a 496 bp product, the c-jun primers, ATGGGCACATCACCACTACACC-3' (SEQ ID NO.4) and 3'-CCAACCTCAGCAACTTCAACCC-5' (SEQ ID NO.5) amplified a 279 bp product, and the Fra2 primers, 5'-CAGAGAGAGAGAAAGAGAGCGAGC-3' (SEQ ID NO.6) and 3'-CATTTTTCTCCAGCCCGTGG-5' (SEQ ID NO.7) amplified a 452 bp product.

Western blotting. Protein was electrophoresed through 10% polyacrylamide gels and transferred to Immobilon-P membranes. Anti-CaMKIV (Transduction Labs, monoclonal, clone 26) was used at 1/1000, anti-CREB, NT (Upstate Biotechnology, polyclonal) at 1/2000, anti-phospho-CREB (Upstate Biotechnology, polyclonal) at 1/1000, and anti-RSK2 (Santa Cruz, monclonal, clone E-1) at 1/250. Signal was formed with the use of horseradish peroxidase-labelled secondary antibodies and the ECL detection system from Amersham.

NFAT translocation. Naïve and memory CD4+ T cells (1×10$^6$ cells/ml) were stimulated in growth media with concanavlin A (con A) at 10 μg/ml. Aliquots of 50 μl were spread onto pre-warmed poly-L-lysine coated slides and incubated at 37° C. in 5% CO$_2$ for 15 min. Cells were then fixed in formalin for 10 min at room temperature, washed in PBS, and permeabilized in −20° C. acetone for 2 min. From this point, immunocytochemistry was carried out using an immunoperoxidase detection system according to the manufacturer's instructions (Vectastain elite ABC kit, Vector Laboratories). The anti-NFATc (Santa Cruz, polyclonal, sc-1149) was used at 1/100.

Results

CaMKIV is highly expressed in thymocytes where it might be predicted to influence T cell development (Hanissian et al, J. Biol. Chem. 268:20055 (1993)). Therefore, before examining CREB-dependent cytokine gene induction in activated T cells, it was first necessary to determine whether formation of mature T cells occurs in CaMKIV−/− mice. The total number of T cells obtained from mutant thymus, spleen, and inguinal lymph node was normal, as was the CD4/CD8 surface marker distribution in each compartment, indicating that mature T cells are present in the CaMKIV−/− mice and are able to reach and survive in the periphery.

An ~90% pure CD4+ T cell-enriched population was obtained from spleen by removing B cells and CD8+ T cells by negative selection. The CD4+-enriched T cell population is comprised of both naïve and memory T cells, each capable of producing cytokines in response to stimulation of the TCR. In order to assay the specific subsets, CD4+ cells were sorted into naïve and memory populations based on L-selectin and CD44 surface marker expression (Bradley et al, J. Immunol. 148:324 (1992), Budd et al, J. Immunol. 138:3120 (1987)). It was first necessary, however, to consider the non-CD4+ T cell contaminates present in this population, which include macrophages, dendritic cells, NK cells, and polymorphonuclear leukocytes. Of these, a subset of NK cells, the NK1.1 cell, raises the most serious concern since it expresses the TCR and can respond to TCR stimulation by producing cytokines. Since NK1.1 cells could potentially interfere with interpretation of CD4+ T cell function, cell sorting was set up to select only those cells negative for the NK1.1 surface marker. When this was carried out, the total number and L-selectin/CD44 staining profiles of wild type and mutant CD4+ T cells appeared similar to previously reported patterns, with approximately 85–90% staining L-selectin$^{high}$/CD44$^{low}$ (naïve T cells) and 10–15% staining L-selectin$^{low}$/CD$_{44}^{high}$ (memory T cells) (Lee et al, Cell. Immunol. 188:1 (1998)). It should be noted that surface marker expression can not definitively differentiate between activated effector and long-lived memory T cells (Lee et al, Cell. Immunol. 188:1 (1998)). Therefore, the L-selectin$^{low}$/CD44$^{high}$ population will be referred to as "memory phenotype CD4+ T cells".

Figure 9A:
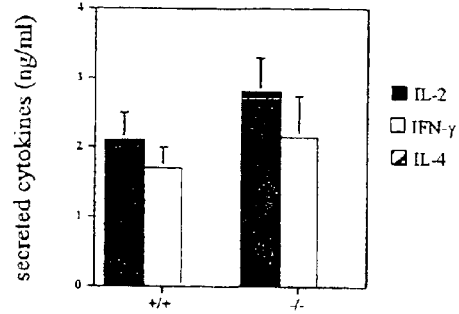
FIGS. 9A–9F. CD4+ memory phenotype T cells from CaMKIV−/− mice exhibit defective cytokine secretion. Following 3 days of stimulation with plate-bound CD3 and CD28 antibodies under neutral conditions, IL-2, IFN-γ, and IL-4 from naïve (FIG. 9A) and memory phenotype (FIG. 9B) CD4+ T cells from wild type or CaMKIV−/− mice were determined. Bars represent mean +/−S. E. where n=5. To assess helper cell differentiation, naïve cells from wild type and CaMKIV−/− mice were primed for 4 days in the presence of recombinant IL-12 and neutralizing IL-4 antibody, which promote Th1 differentiation (FIG. 9C), or with recombinant IL-4 to promote Th2 differentiation (FIG. 9D). The cells were then pelleted, washed, and restimulated for 1 day, at the end of which period secreted cytokines were determined. Bars represent mean +/− S.E. where n=3. Over the time course in which cytokine secretion was measured, cell proliferation, as assessed by [3H]thymidine incorporation (FIG. 9E), and cell survival, based on trypan blue exclusion (FIG. 9F), were determined. Bars represent mean +/− S.E. where n=3 (FIG. 9E) or n=7 (FIG. 9F).

The naïve T cells were assayed for IL-2 production after TCR stimulation with CD3 and CD28 antibodies under neutral conditions. The wild type and mutant cells were found to secrete similar levels of IL-2, indicating that CaMKIV is not required for production of this cytokine (FIG. 9A). However, when memory phenotype T cells were stimulated with CD3 and CD28 antibodies, the CaMKIV-/- cells were found to secrete 8 fold less IL-2 than wild type (FIG. 9B), indicating a possible functional defect in this T cell subset.

Figure 9B:
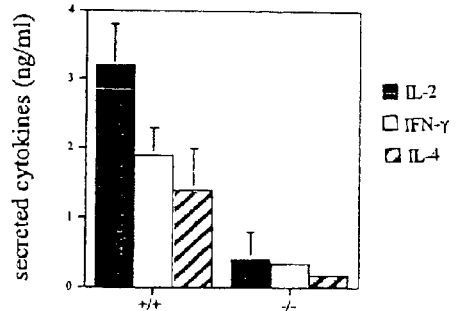
Figure 9C:
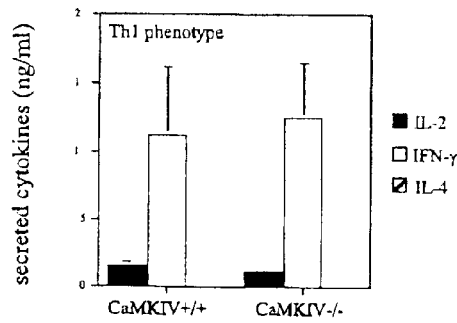
Figure 9D:
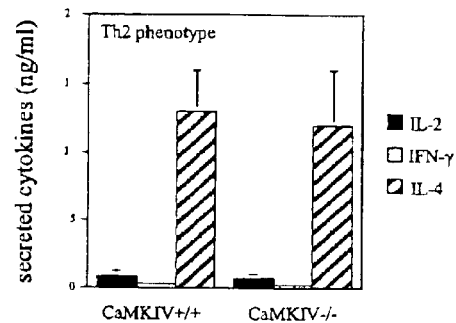
Figure 9E:
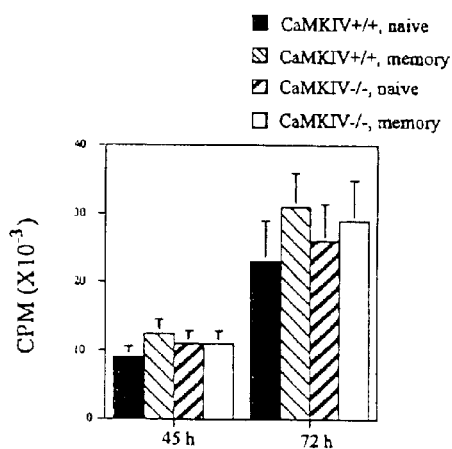
Figure 9F:
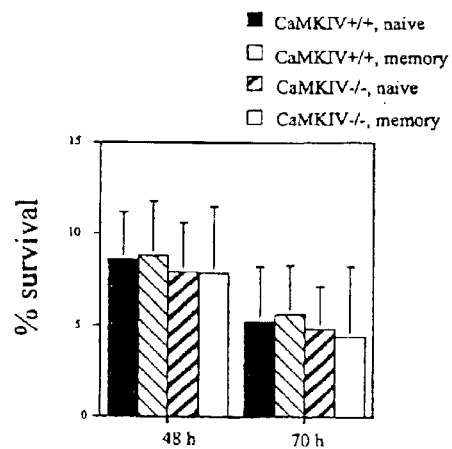

One of the distinguishing characteristics of memory T cells is their ability, collectively, to produce and secrete a broad range of cytokines. To determine whether the impaired cytokine production of the mutant was specific to IL-2, two other cytokines were examined. IFN-γ and IL-4 secretion from stimulated memory phenotype cells were reduced 5 and 8 fold, respectively, in cells from CaMKIV-/- mice (FIG. 9B). Next, to determine whether the impaired IFN-γ and IL-4 production was specific to the memory phenotype T cell subset, naïve cells were assayed for these cytokines. Stimulation by CD3 and CD28 antibodies, again under neutral conditions, led to a moderate level of IFN-γ secretion from both mutant and wild type naïve cells, while IL-4 secretion was not detectable from either (FIG. 9A). One distinguishing property of naïve T cells is their ability to differentiate into Th1 or Th2 effector cells. Th1 effectors are defined by their tendency to produce large quantities of Th1 cytokines, including IFN-γ, while Th2 effectors selectively produce Th2 cytokines, such as IL-4. When cytokine production was determined following a 4 d priming period under conditions that favor Th1 differentiation, naïve cells from wild type and mutant mice produced similarly high levels of IFN-γ and no detectable IL-4 (FIG. 9C). Priming of naïve cells under conditions that promote Th2 differentiation led to the secretion of high amounts of IL-4 and low IFN-γ (FIG. 9D). Again, there was no significant difference in cytokine production between wild type and mutant naïve cells. In summary, stimulated naïve T cells from CaMKIV-/- mice secrete normal levels of IL-2, IL-4, and IFN-γ, while the memory phenotype cells show impaired production of all three cytokines. FIG. 9 also demonstrates that stimulated naïve and memory phenotype cells from CaMKIV-/- mice display normal proliferation (FIG. 9E) and cell survival (FIG. 9F) over the time course in which cytokine production was measured. Thus, the diminished cytokine secretion by mutant memory phenotype cells is not due to increased apoptosis or to the failure of the cells to proliferate.

Figure 10:
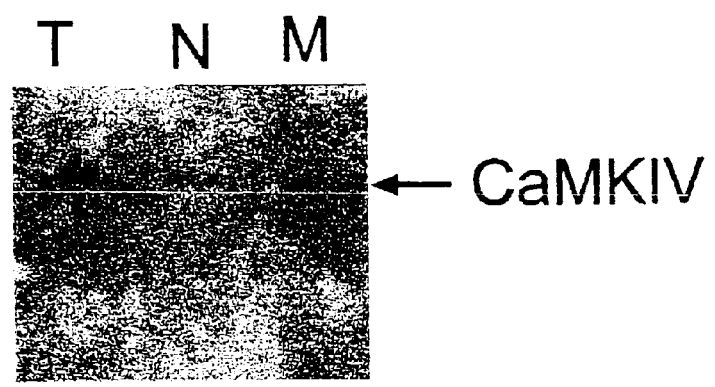
FIG. 10. CaMKIV is expressed in CD4+ naïve and memory phenotype T cells. CaMKIV protein expression was detected in thymocytes and in CD4+ naïve and memory phenotype T cells by western blotting of whole cell lysates made from 0.3×10$^6$ cells. For each cell type the entire lysate was used in the assay, so that signals from equivalent numbers of cells are being compared. Shown is one representative experiment where n=2.
Figure 11A:
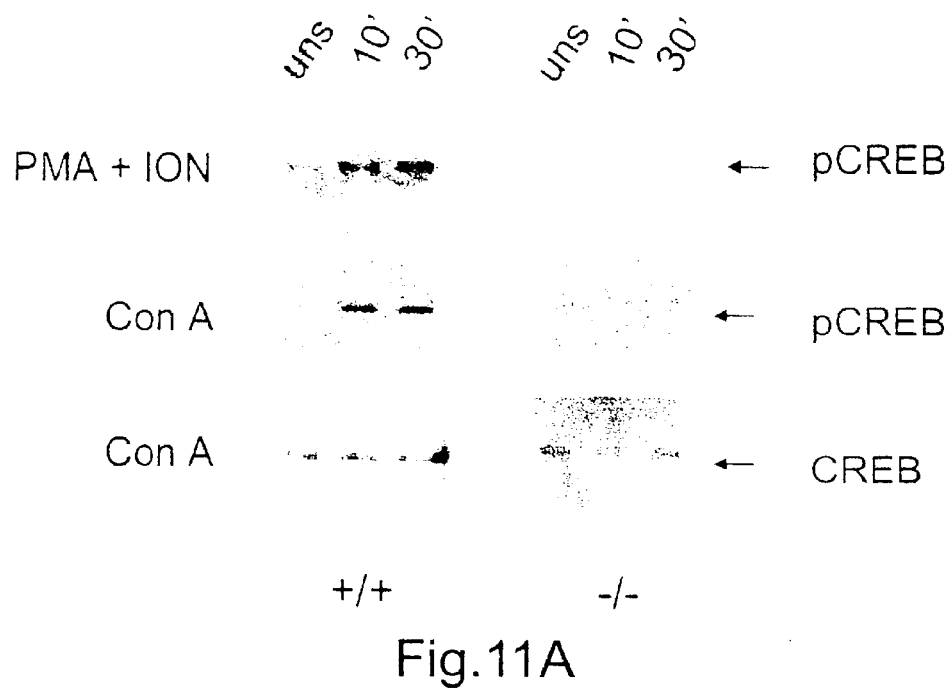
FIGS. 11A and 11B. Stimulated CD4+ memory phenotype T cells from CaMKIV−/− mice display impaired CREB phosphorylation. The inducible CREB phosphorylation in CD4+ memory phenotype (FIG. 11A) and naïve (FIG. 11B) T cells from wild type and CaMKIV−/− mice was determined by western blotting with antibody against CREB phosph-serine 133 (upper two panels of FIGS. 11A and 11B). Cells were either unstimulated or stimulated with 10 ng/ml PMA plus 1 μM ionomycin or with 10 μg/ml concanavalin A for 10 and 30 min. Blotting with antibody against total CREB is shown in the lower panels of FIGS. 11A and 11B. Shown is one representative experiment where n=6.
Figure 11B:
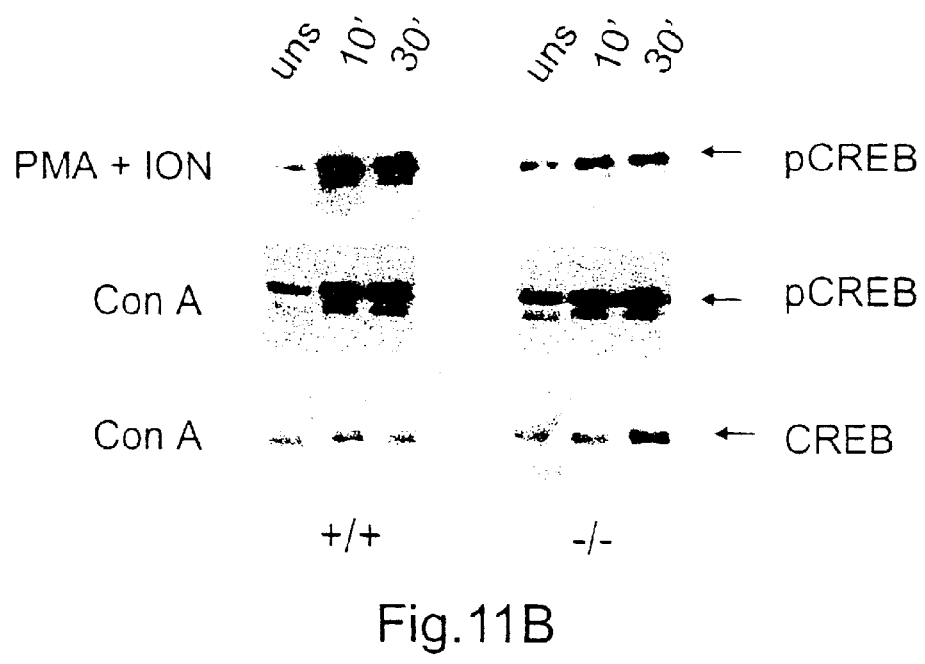

It was next determined whether the functional defect exhibited by the memory phenotype T cells was due to an acute signaling problem downstream of the TCR. Although CaMKIV expression in thymocytes and unfractionated CD4+ T cells has been previously reported, the presence of the kinase in memory cells was not examined (Frangakis et al, J. Biol. Chem. 266:17592 (1991), Hanissian et al, J. Biol. Chem. 268:20055 (1993)). FIG. 10 shows that CaMKIV is expressed in both naïve and memory phenotype CD4+ T cells. Based on the properties of CaMKIV, the most likely direct target of the kinase capable of influencing cytokine production is CREB Ser133. CREB phosphorylation in CaMKIV-/- memory phenotype T cells following acute stimulation with either PMA and ionomycin or with ConA was found to be dramatically reduced compared with cells from wild type animals (FIG. 11B). In contrast, the inducible CREB phosphorylation in naïve T cells from CaMKIV-/- mice was similar to that observed in cells from wild type animals (FIG. 11B).

Figure 12A:
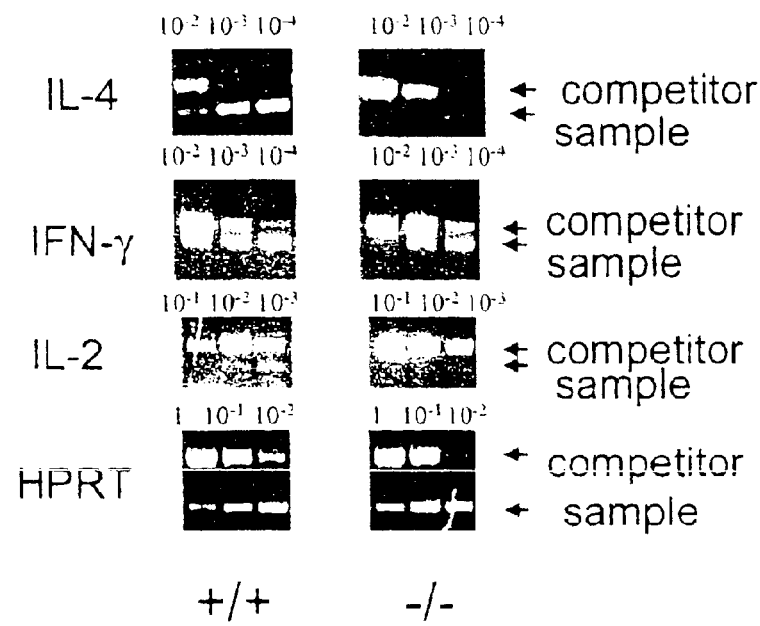
FIGS. 12A and 12B. CD4+ memory phenotype T cells from CaMKIV−/− mice display impaired cytokine gene induction. CD4+ memory phenotype (FIG. 12A) and naïve (FIG. 12B) T cells from wild type and CaMKIV−/− mice were stimulated with plate-bound CD3 and CD28 antibodies for 2 days. Total RNA was then isolated and IL-2, IFN-γ, and IL-4 gene induction measured by competitive RT-PCR, as described. The numbers above the lanes indicate the pmoles of competitor construct included in the PCR reaction. For each of the 4 genes examined, the PCR product arising from the competitor construct (upper arrow) runs higher in the gel compared to that from the endogenous gene (lower arrow). Shown is one representative experiment where n=4.
Figure 12B:
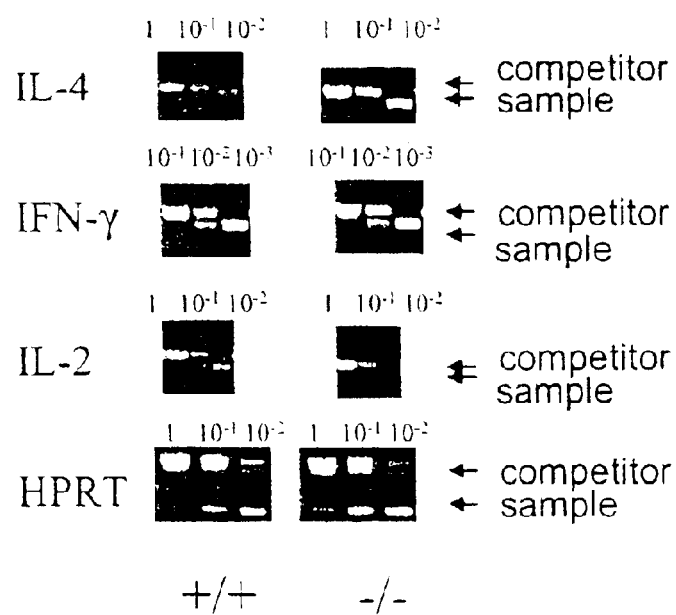

The decreased CREB phosphorylation and cytokine secretion observed in mutant memory phenotype cells suggested that immediate early gene (IEG) and cytokine gene induction would also be impaired. To determine whether cytokine gene induction was impaired, mRNA levels were indirectly measured using semi-quantitative RT-PCR. The IL-4 cDNA from the mutant memory phenotype cells could be competed by 10–100 fold less competitor DNA compared to wild type, indicating 10–100 fold less IL-4 mRNA induction in the mutant (FIG. 12A). The IL-2 and IFN-γ mRNA levels in the mutant memory phenotype cells were also reduced, each by approximately 10 fold compared to wild type. Not shown are signals from unstimulated cells which were always undetectable. Consistent with their ability to produce normal amounts of cytokines, the mutant naïve T cell mRNA levels were similar to wild type (FIG. 12B).

Figure 13:
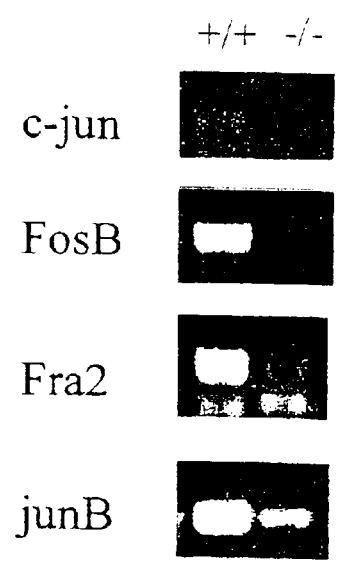
FIG. 13. CD4+ memory phenotype T cells from CaMKIV−/− mice display impaired immediate early gene induction. CD4+ memory phenotype T cells from wild type and CaMKIV−/− mice were stimulated with plate-bound CD3 and CD28 antibodies for 2 h. Total RNA was then isolated and c-jun, FosB, Fra2, and junB gene induction determined by RT-PCR. Shown is one representative experiment where n=4.

A number of IEGs implicated in cytokine gene induction, including c-jun, JunB, FosB, and Fra2, require CREB phosphorylation for their induction (Barton et al, Nature 379:81 (1996), Glimcher et al, Cell 96:13 (1999), Rooney et al, Immunity 2:473 (1995)). The induction of these genes in mutant memory phenotype cells was examined by RT-PCR. C-jun mRNA was undetectable and Jun B, Fos B, and Fra 2 were markedly reduced (FIG. 13).

Figure 14:
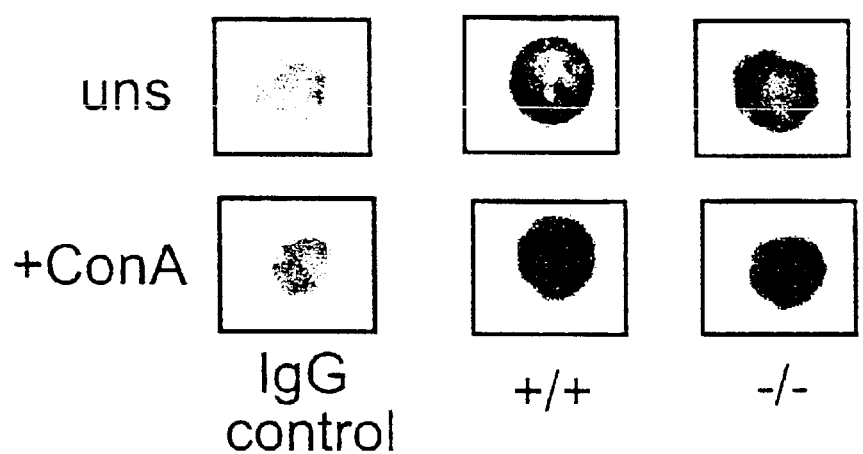
FIG. 14. NFAT (nuclear factor of activated T cells) translocation in CD4+ memory phenotype T cells from CaMKIV−/− mice is normal. CD4+ memory phenotype T cells from wild type and CaMKIV−/− mice were either unstimulated or stimulated for 15 min with concanavalin A. NFAT subcellular localization was then determined by immunocytochemistry. In the control, anti-mouse IgG was substituted for anti-NFAT. Shown are representative cells from a single experiment, repeated 2 times. Magnification is 1000×.

The results described thus far indicate that CaMKIV is required for the Ca$^{2+}$-dependent CREB phosphorylation that leads to IEG and cytokine gene induction in stimulated memory phenotype cells. To verify that the Ca$^{2+}$ signal upstream of CaMKIV is functional in the mutant cells, NFAT translocation was examined. NFAT translocation from cytoplasm to nucleus is a major Ca$^{2+}$-dependent pathway critical in stimulated T cells. Immunostaining demonstrates that the movement of NFAT from the cytoplasm to the nucleus occurs in stimulated memory phenotype cells from mutant mice (FIG. 14).

Figure 15:
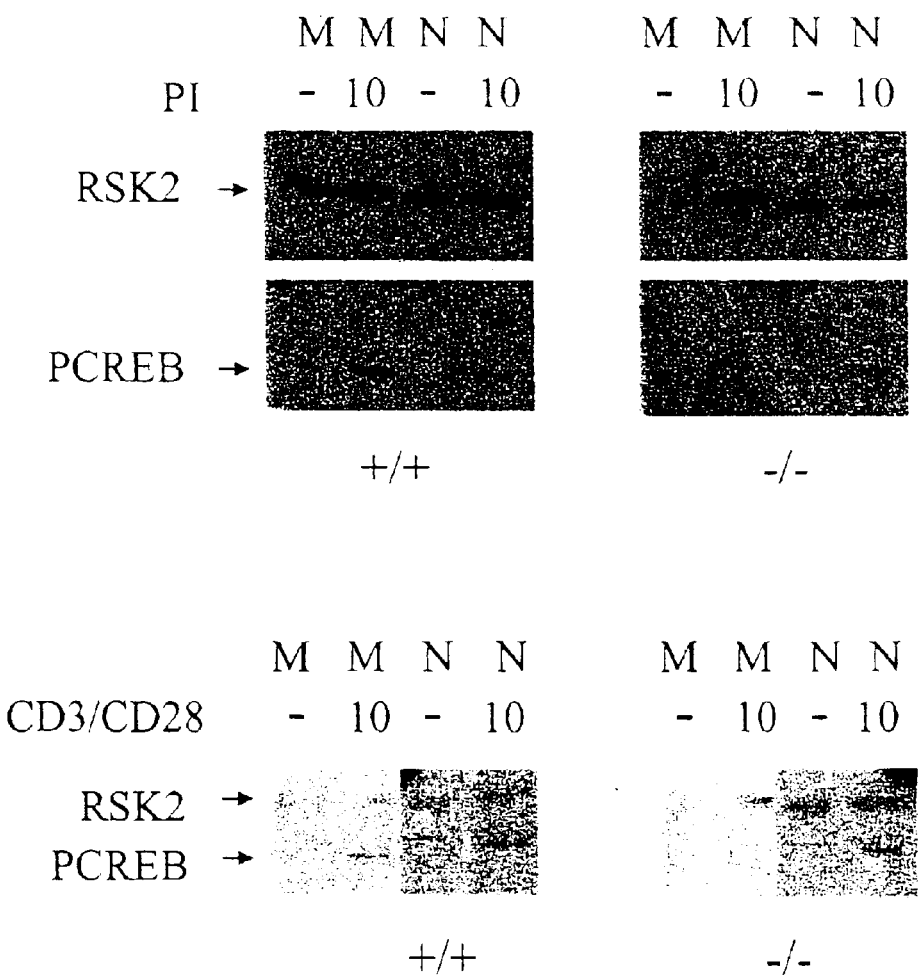
FIG. 15. Expression and activation of RSK2 in CD4+ T cells. Naïve (N) and memory phenotype (M) CD4+ T cells from wild type and CaMKIV−/− mice were probed for RSK2 and for phospho CREB by western blot after stimulation with PMA (10 ng/ml) and ionomycin (1 µM) (PI) (upper panels) or CD3/CD28 (lower panels) for 10 min. Activated RSK2 appears as a slower migrating band.

It is curious that memory phenotype, but not naïve, T cells from CaMKIV-/- mice show a CREB phosphorylation signaling defect. RSK2 has been reported to phosphorylate CREB in unfractionated T cells and in lymphocyte derived cell lines, but has not been examined in purified naïve and memory cells. Perhaps the RSK2 pathway is restricted to the naïve T cell where it regulates CREB phosphorylation, but is absent in the memory cell leaving CaMKIV the sole $Ca^{2+}$-dependent CREB kinase in this T cell subtype. To test this possibility, the presence and activation of RSK2 were assayed by western blot in naïve and memory phenotype T cells from wild type and CaMKIV−/− mice. FIG. 15 demonstrates that RSK2 is present in both wild type naïve and memory phenotype T cells and that it undergoes the expected shift to a slower migrating, activated form in response to cell stimulation. Shown also is the expected phosphorylation of CREB in response to cell stimulation. RSK2 is present and activatable in naïve and memory phenotype T cells from CaMKIV−/− mice as well, although CREB phosphorylation is not detectable in the stimulated memory phenotype cells (FIG. 15). This later result indicates that although present, RSK2 activation is not coupled to CREB phosphorylation in the memory cell.

All documents cited above are hereby incorporated in their entirety by reference.

One skilled in the art will appreciate from a reading of this disclosure that various changes in form and detail can be made without departing from the true scope of the invention.

What is claimed is:

1. A method of screening a test compound for CaMKIV agonist activity comprising:
   i) contacting CaMKIV and a substrate therefor, in the presence and absence of the test compound, under conditions such that CaMKIV-dependent phosphorylation of said substrate can be effected, and
   ii) determining the level of phosphorylation of said substrate resulting from step (i) and comparing said level with a level of phosphorylation of said substrate in the absence of said test compound,
   wherein an increase in phosphorylation of said substrate in the presence of said test compound indicates that said test compound is a CaMKIV agonist.

2. The method according to claim 1 wherein said substrate is a peptide substrate.

3. The method according to claim 1 wherein said CaMKIV and said substrate are present in a cell free system.

4. The method according to claim 1 wherein said CaMKIV and said substrate are present in a cell.

5. The method according to claim 1 wherein, in step (i), said CaMKIV and said substrate therefor are contacted with said test compound in the presence of CaMKIV kinase, calmodulin and calcium under conditions such that CaMKIV kinase dependent phosphorylation of CaMKIV can be effected.

6. A method of screening a test compound for its activity to inhibiting differentiation of CD4+ T cells into Th2 cells comprising:
   i) contacting CaMKIV and a substrate therefor in the presence of said test compound, under conditions such that CaMKIV-dependent phosphorylation of said substrate can be effected, and
   ii) determining the level of phosphorylation of said substrate resulting from step (i) and comparing said level with a level of phosphorylation of said substrate obtained in the absence of said test compound,
   wherein a reduction in the level of phosphorylation of said substrate in the presence of said test compound indicates that said test compound has said activity to inhibit differentiation of CD4+ T cells into Th2 cells.

7. The method according to claim 6 wherein said substrate is a peptide substrate.

8. The method according to claim 6 wherein said CaMKIV and said substrate are present in a cell free system.

9. The method according to claim 6 wherein said CaMKIV and said substrate are present in a cell.

10. The method according to claim 6 wherein, in step (i), said CaMKIV and said substrate therefor are contacted with said test compound in the presence of CaMKIV kinase, calmodulin and calcium under conditions such that CaMKIV kinase dependent phosphorylation of CaMKIV can be effected.

11. A method of screening a test compound for enhance hematopoietic cell differentiation comprising:
   i) contacting CaMKIV and a substrate therefor in the presence of said test compound, under conditions such that CaMKIV-dependent phosphorylation of said substrate can be effected, and
   ii) determining the level of phosphorylation of said substrate resulting from step (i) and comparing said level with a level of phosphorylation of said substrate obtained in the absence of said test compound,
   wherein an increase in the level of phosphorylation of said substrate in the presence of said test compound indicates that said test compound has said activity to enhance hematopoietic cells differentiation.

12. The method according to claim 12 wherein said substrate is a peptide substrate.

13. The method according to claim 12 wherein said CaMKIV and said substrate are present in a cell free system.

14. The method according to claim 12 wherein said CaMKIV and said substrate are present in a cell.

15. The method according to claim 12 wherein, in step (i), said CaMKIV and said substrate therefor are contacted with said test compound in the presence of CaMKIV kinase, calmodulin and calcium under conditions such that CaMKIV kinase dependent phosphorylation of CaMKIV can be effected.

* * * * *